United States Patent [19]

Bowie et al.

[11] 3,961,696
[45] June 8, 1976

[54] DEVICE FOR MAKING A CULTURE OF $CO_2$ REQUIRING ORGANISMS

[75] Inventors: Betty Anne Bowie, Havertown; Joseph F. Pagano, Paoli, both of Pa.

[73] Assignee: SmithKline Corporation, Philadelphia, Pa.

[22] Filed: Oct. 20, 1975

[21] Appl. No.: 623,936

[52] U.S. Cl. .............................................. 195/139
[51] Int. Cl.² ........................................ C12B 1/02
[58] Field of Search ...................... 195/139, 103.5 R

[56] References Cited
UNITED STATES PATENTS

| | | |
|---|---|---|
| 3,616,263 | 10/1971 | Anandam..................... 195/139 X |
| 3,616,265 | 10/1971 | Calabrese et al. ................. 195/139 |
| 3,862,013 | 1/1975 | Pagano .............................. 195/139 |
| 3,888,741 | 6/1975 | Freake et al....................... 195/139 |

*Primary Examiner*—A Louis Monacell
*Assistant Examiner*—Robert J. Warden
*Attorney, Agent, or Firm*—Smith, Harding, Earley & Follmer

[57] ABSTRACT

A device for making a culture of carbon dioxide ($CO_2$) requiring organisms has an elongated member supporting a culture medium in a container having an open end which is adapted to be closed by sealing means. A $CO_2$ tablet is secured to the elongated member between the culture medium and the open end of the container.

6 Claims, 10 Drawing Figures

U.S. Patent    June 8, 1976    3,961,696
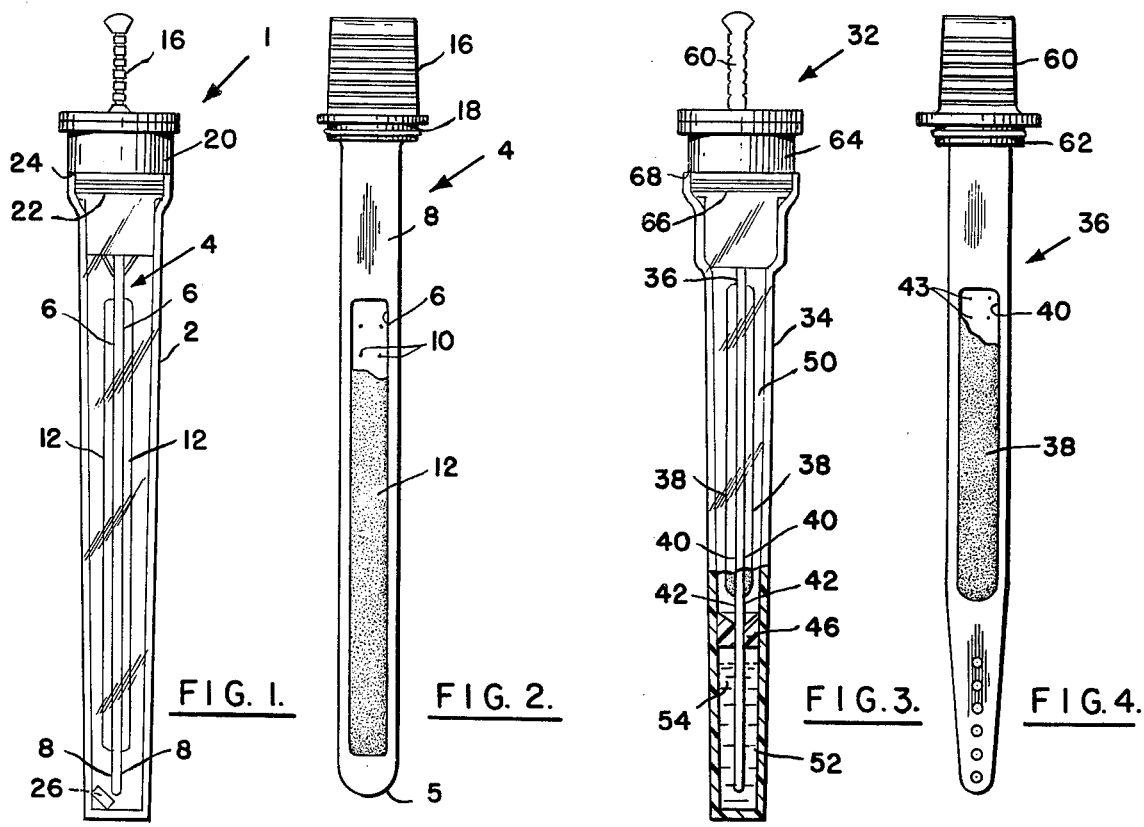
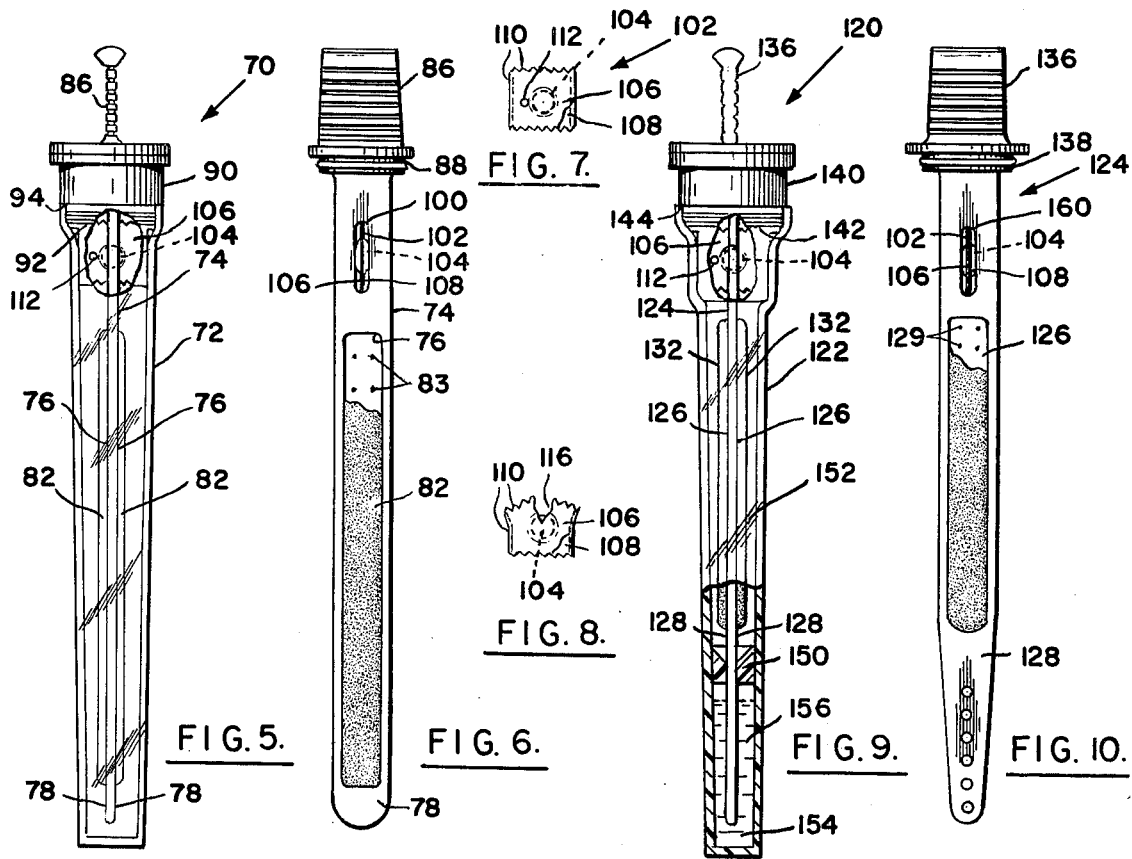

DEVICE FOR MAKING A CULTURE OF CO₂ REQUIRING ORGANISMS

BACKGROUND OF THE INVENTION

It is known to culture Neisseria gonorrhoeae and other $CO_2$ requiring organisms in a culture medium retained on an elongated member which is removably positioned in a closed container such as is shown in U.S. Pat. No. 3,616,265. It is known to the art to employ a carbon dioxide ($CO_2$) tablet usually containing sodium bicarbonate and an organic acid, such as citric acid, in the bottom of the container to provide carbon dioxide which is desired to facilitate the culturing of the organism. In the presence of moisture the tablet releases $CO_2$. Considerable difficulty has been experienced due to the fact that the amount of moisture available to the tablet varies greatly. Frequently, excessive moisture condenses in the container forming a pool of water surrounding the tablet causing a rapid evolution of carbon dioxide within minutes producing a higher than usual pressure and a greater leakage through the closure and reducing the length of time that carbon dioxide is present in the container to an unsatisfactory time period. This difficulty is remedied by the invention by providing means to secure a $CO_2$ tablet to the elongated member supporting the culture medium at a point between the culture medium and the open end of the container to positively prevent the tablet from being exposed to an accumulation of water. This results in a relatively even release of carbon dioxide due to the interaction of moisture in the air within the container and the tablet assuring the presence of carbon dioxide within the container for a period of time sufficient to carry out the desired culturing, for example, 2 days.

SUMMARY OF THE INVENTION

A device for making a culture of $CO_2$ requiring organisms has an elongated member supporting a culture medium in a container having an open end which is adapted to be closed by sealing means. A $CO_2$ tablet is secured to the elongated member between the culture medium and the open end of the container.

DESCRIPTION OF THE DRAWING

FIG. 1 is a side elevation of a single chamber culture device known to the prior art;

FIG. 2 is a front elevation of the elongated culture medium supporting member of the device in FIG. 1;

FIG. 3 is a side elevation of a two chamber culture device known to the prior art;

FIG. 4 is a front elevation of the elongated culture medium supporting member of the device in FIG. 3;

FIG. 5 is a side elevation of a single chamber culture device in accordance with the invention;

FIG. 6 is a front elevation of the elongated culture medium supporting member of the device in FIG. 5;

FIG. 7 is a plan view of a carbon dioxide tablet packet;

FIG. 8 is a side view of the packet of FIG. 7 showing it torn to expose the tablet to the atmosphere;

FIG. 9 is a side elevation of a double chamber culture device in accordance with the invention; and FIG. 10 is a front elevation of the elongated culture medium supporting member of the device of FIG. 9.

DESCRIPTION OF PRIOR ART

There is shown in FIG. 1 a culture device 1 known to the prior art. The device 1 has a transparent container 2 of, for example, glass or plastic. An elongated member 4 has an inner end 5 and a recessed portion 6 in each opposed substantially flat face 8. Each recessed portion 6 is intermediate the ends of the elongated member 4 and has multiple small protrusions 10 to facilitate the retention of a body 12 of a solid culture medium in the recessed portions. The elongated member 4 has a handle 16 and a plug portion 18 which is adapted to be sealingly engaged within cylindrical member 20 which has a plug portion 22 received within the open end 24 of container 2. Such a container is disclosed in detail in U.S. Pat. No. 3,616,265, the disclosure of which is incorporated herein by reference. When organisms are being cultured, it is known to introduce into the bottom of container 2 a carbon dioxide tablet 26.

It is also known to employ a double chamber culture device such as that shown at 32 in FIG. 3. The device 32 has a transparent container 34 containing an elongated member 36 which supports a culture medium 38 in recesses indicated at 40, 40 in opposite faces 42, 42 of the elongated member 36 and having protrusions 43. Elongated member 36 extends through a ring seal 46 which together with the elongated member 36 separates container 34 into two separate compartments 50 and 52. Chamber 52 contains a liquid culture medium 54. Elongated member 36 has a handle 60 and a plug portion 62 which sealingly engages a cylindrical member 64 which, in turn, has a plug portion 66 which sealingly engages the open end 68 of container 34. Culture devices such as the device 32 have not been employed where it is desired to have carbon dioxide in the upper chamber 50 due to the difficulty of providing a carbon dioxide tablet in chamber 50.

DETAILED DESCRIPTION OF INVENTION EMBODIMENTS

A culture device 70 in accordance with the invention has a transparent container 72 containing an elongated member 74 with recesses 76, 76 in opposite faces 78, 78 containing culture medium 82 and protrusions 83. Elongated member 74 has a handle 86 and a plug portion 88 which sealingly engages a cylindrical member 90 which, in turn, has a plug portion 92 mounted in the open end 94 of container 72. As thus described the device 70 is the same as the device 1. Elongated member 74 has a slot 100 in which there is secured a packet 102 containing a carbon dioxide tablet 104. Packet 102 may be, for example, opposed sheets 106 and 108 of a plastic such as cellophane, polyethylene or polypropylene, or a metal foil such as aluminum or tinfoil heat sealed at its edges 110 to be air tight or a combination thereof. Such packets are well known to the art and hence need not be described in greater detail. $CO_2$ tablets are also well known. Typically the $CO_2$ tablet 104 will contain a carbonate such as sodium bicarbonate and a water soluble organic acid, such as citric acid or tartaric acid. $CO_2$ tablets are available commercially, for example, "TAB-$CO_2$" sold by Ames Company Inc., 1127 Myrtle Street, Elkhart, Indiana. As shown in FIG. 7 the packet is activated by punching a pinhole 112 in sheet 106 to provide for the admission of air and moisture within packet 102 to the $CO_2$ tablet 104 and the exit of the formed carbon dioxide. As best seen in FIG. 6, slot 100 is sized to provide for a wedged fit of the packet 102.

In operation, the sealed packet 102 is punctured with pin opening 112 and then the packet is securely wedged in slot 100. The specimen suspected of having the micro-organism in question is brought into contact with the culture medium 82 and the elongated member 74 is placed in container 72. If a somewhat faster release of $CO_2$ is desired, the packet 102 can be provided with a tear 116 adjacent the tablet 104 as illustrated in FIG. 8.

Referring now to FIG. 9, a two compartment culture device 120 has a transparent container 122 containing an elongated member 124 with recesses 126 in opposite faces 128, 128 containing culture medium 132 and protrusions 129. Elongated member 124 has a handle 136 and a plug portion 138 which sealingly engages a cylindrical member 140 which, in turn, has a plug portion 142 which engages the open end 144 of container 122. Elongated member 124 passes downwardly through a seal ring 150 which separates container 122 into upper compartment 152 and a lower compartment 154 containing a liquid culture medium 156. As thus described the culture device 120 is the same as culture device 32 shown in FIG. 3.

Elongated member 124 has a slot 160 which is sized to receive and hold by a wedged fit a packet 102 containing a $CO_2$ tablet 104.

In operation, the elongated member 124 is removed from the container 122 while holding the container in a vertical position to retain the liquid culture medium 156 in compartment 154. The container is placed in a holder to maintain it vertical and the packet is pierced to provide opening 112 and then securely wedged in slot 160. The selected specimens are then placed on the lower end of elongated member 124 for introduction into the liquid culture medium 156 and on culture medium 126 for culturing in compartment 152 in the presence of carbon dioxide. Elongated member 124 is then replaced in container 122. After a suitable period of incubation the doctor will make his observation through the transparent walls of the container 122.

A typical solid culture medium for use in the invention to culture Neisseria gonorrhoeae is disclosed by Martin, J. E., Jr. and Lester, A. In HSMHA Health Reports, Volume 86, pages 30 –33, 1971.

Exemplary of a $CO_2$ tablet is a tablet made with a 3/16 inch punch and having the following composition:

| | |
|---|---|
| Citric Acid (U.S.P.) anhydrous granular) | 21.320 mg. |
| Sodium Bicarbonate (U.S.P.) | 28.000 mg. |
| Terra Alba (U.S.P.) | 8.650 mg. |
| Magnesium Stearate (U.S.P.) | 0.073 mg. |

Carbon dioxide within the culturing container is desirable when culturing micro-organisms contained in body liquids. Typical of such micro-organisms are Neisseria gonorrhoeae and streptococci.

It is not desired to be limited except as set forth in the following claims:

We claim:

1. A device for making a culture of micro-organisms comprising:
    an elongated member,
    a culture medium for culturing $CO_2$ requiring organisms supported by said member,
    a container for the elongated member having an open end,
    means to seal the open end of the container, and
    means to secure a $CO_2$ tablet to said elongated member between the culture medium and the open end of the container with the tablet exposed to the atmosphere within the container.

2. A device in accordance with claim 1 in which the means to secure the tablet comprises an opening in the elongated member and a packet for the tablet received in the opening.

3. A device in accordance with claim 1 in which the tablet contains sodium bicarbonate and citric acid.

4. A device in accordance with claim 2 in which the tablet contains sodium bicarbonate and citric acid.

5. A device in accordance with claim 2 in which the packet has a pinhole opening adjacent the tablet.

6. A device in accordance with claim 2 in which the packet has a tear adjacent the tablet.

* * * * *